US005391158A

United States Patent [19]

Peters

[11] Patent Number: 5,391,158

[45] Date of Patent: Feb. 21, 1995

[54] NASOGASTRIC TUBE

[76] Inventor: Michael J. Peters, 2196 Wycliffe, West Bloomfield, Mich. 48323

[21] Appl. No.: 201,556

[22] Filed: Feb. 24, 1994

[51] Int. Cl.[6] .................... A61M 25/00; A61M 31/00

[52] U.S. Cl. .................................... 604/265; 604/270

[58] Field of Search ................ 604/54, 164, 170, 270, 604/280; 128/657, 772

[56] References Cited

U.S. PATENT DOCUMENTS

| | | | |
|---|---|---|---|
| 3,155,097 | 11/1964 | Barron | 604/270 |
| 3,395,710 | 8/1968 | Stratton et al. | 604/270 |
| 4,318,402 | 3/1982 | Vaillancourt | 604/280 |
| 4,485,805 | 12/1984 | Foster, Jr. | 604/54 |

FOREIGN PATENT DOCUMENTS

| | | | |
|---|---|---|---|
| 0591963 | 7/1925 | France | 604/270 |

*Primary Examiner*—John D. Yasko
*Assistant Examiner*—Adam J. Cermak
*Attorney, Agent, or Firm*—Lyman R. Lyon

[57] ABSTRACT

A system for introducing a nasogastric tube into the stomach of a patient comprises a digestible weight capable of being swallowed by the patient, a digestible guide string having one end attached to the weight, and a tube telescoped about the guide string for guidance thereby into the stomach of said patient.

3 Claims, 1 Drawing Sheet

NASOGASTRIC TUBE

BACKGROUND OF THE INVENTION

The present invention relates to apparatus for introducing and evacuating fluids to and from the stomach and more specifically to a nasogastric tube system which minimizes damage to tissue during insertion.

Gastric tubes are used for introducing fluids into the stomach and evacuating fluids from the stomach. Most gastric tubes are nasogastric tubes, i.e., they are inserted through the nose rather than the mouth in order to avoid gagging the patient. Nasogastric tubes pass through the nostril, nasopharynx, oropharynx, and esophagus and into the stomach.

The commonly-used nasogastric tube is difficult to negotiate through the nasal passageways into the esophagus. The current practice of inserting the tube by force through the nasal passageways without guide apparatus tears and abrades tissues in the nostril and nasopharynx and causes the patient discomfort. Furthermore, if the tube is inadvertently inserted past the epiglottis and into the trachea instead of the esophagus, the patient's larynx, or vocal cords, could be damaged by the tube.

Other known methods for inserting a nasogastric tube use a weight connected by a string to the end of the tube. The weight is inserted through the nostril to the nasopharynx, after which it is swallowed. Peristaltic action of the involuntary muscles of the esophagus forces the weight downwardly. The nasogastric tube is drawn downwardly by the string. However, one problem with inserting a nasogastric tube with an attached weight is that involuntary muscle action in the esophagus will swallow the weight and draw the tube through the nostril, nasopharynx, oropharynx, and esophagus rapidly and uncontrollably. If the tube impinges tissue in the passageways, the tube will tear or abrade the tissue as it is drawn by the peristaltic action of the involuntary muscles acting on the weight.

Another problem with this known method is that the weight is difficult to retrieve. The weight is either permanently attached to the tube or disconnected before withdrawal of the tube. If the weight is permanently attached to the tube, it must be pulled back up through the digestive tract when the tube is removed. Pulling the weight up through the digestive tract and out the nostril tears tissue and causes severe discomfort to the patient. If the weight is disconnected before withdrawal of the nasogastric tube, the weight must pass intact through the digestive system because it is not digestible.

SUMMARY OF INVENTION

The aforesaid problems are solved, in accordance with a preferred embodiment of the present invention, by a system for evacuating and administering fluids in and to the stomach, respectively, comprising a digestible weight, a digestible guide string, and a nasogastric tube of unique configuration.

In the preferred embodiment, a digestible, "hot dog" shaped weight is connected to a digestible guide string and inserted through the patient's nostril to the nasopharynx, where it is swallowed by the patient. The free end of the guide string is maintained exteriorly of the patient's nasopharynx while the weight is swallowed while the attachment end of the guide string is routed through the nose, nasopharynx, oropharynx, and esophagus to the stomach.

In accordance with one feature of the invention, the nasogastric tube is closed at a conical insertion end except for a string hole which facilitates its travel through the passageways to the stomach. The tube has apertures adjacent its insertion end for drainage and administration of fluid in the stomach.

The free end of the guide string is inserted through the hole in the insertion end of the nasogastric tube and threaded through the tube. After the nasogastric tube is inserted into the nostril it is guided by the guide string through the passageways into the stomach. The tube passes through the nasopharynx without impinging tissue on the side walls and into the esophagus without damaging the vocal cords because the tube follows the guide string and because the conical insertion end of the tube does not abrade surrounding tissue. After removing the nasogastric tube, the guide string is swallowed and the weight and guide string are digested safely and comfortably.

DETAILED DESCRIPTION OF THE PREFERRED EMBODIMENT

Figure 1:
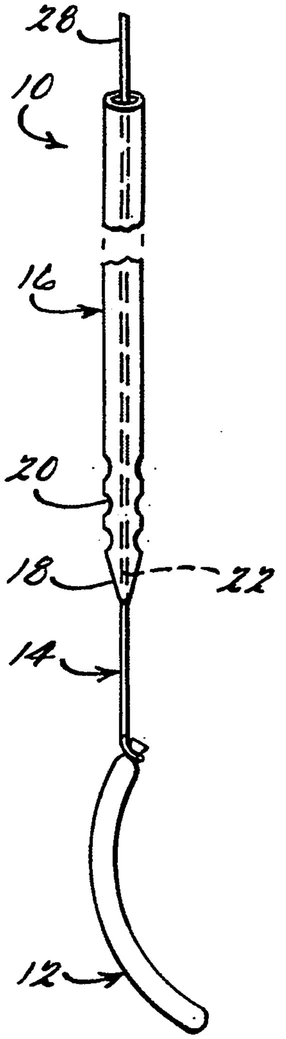
FIG. 1 is an illustration of the preferred embodiment of the system which comprises a nasogastric tube, weight, and guide string.

The preferred system 10 for introducing and evacuating fluids to and from the stomach, in accordance with the present invention, is shown in FIG. 1. A weight 12, comprises a hot dog shaped digestible balloon, approximately 3 inches long and ¼ inch wide, that is filled with water. The weight 12 is attached to a guide string 14 which is also made of a digestible material, such as catgut.

A nasogastric tube 16 has a conical insertion end 18 with apertures 20 near the insertion end 18 for the passage of fluids. A guide aperture 22 is provided at the tip of the insertion end 18 for the acceptance of the string 14.

Figure 2:
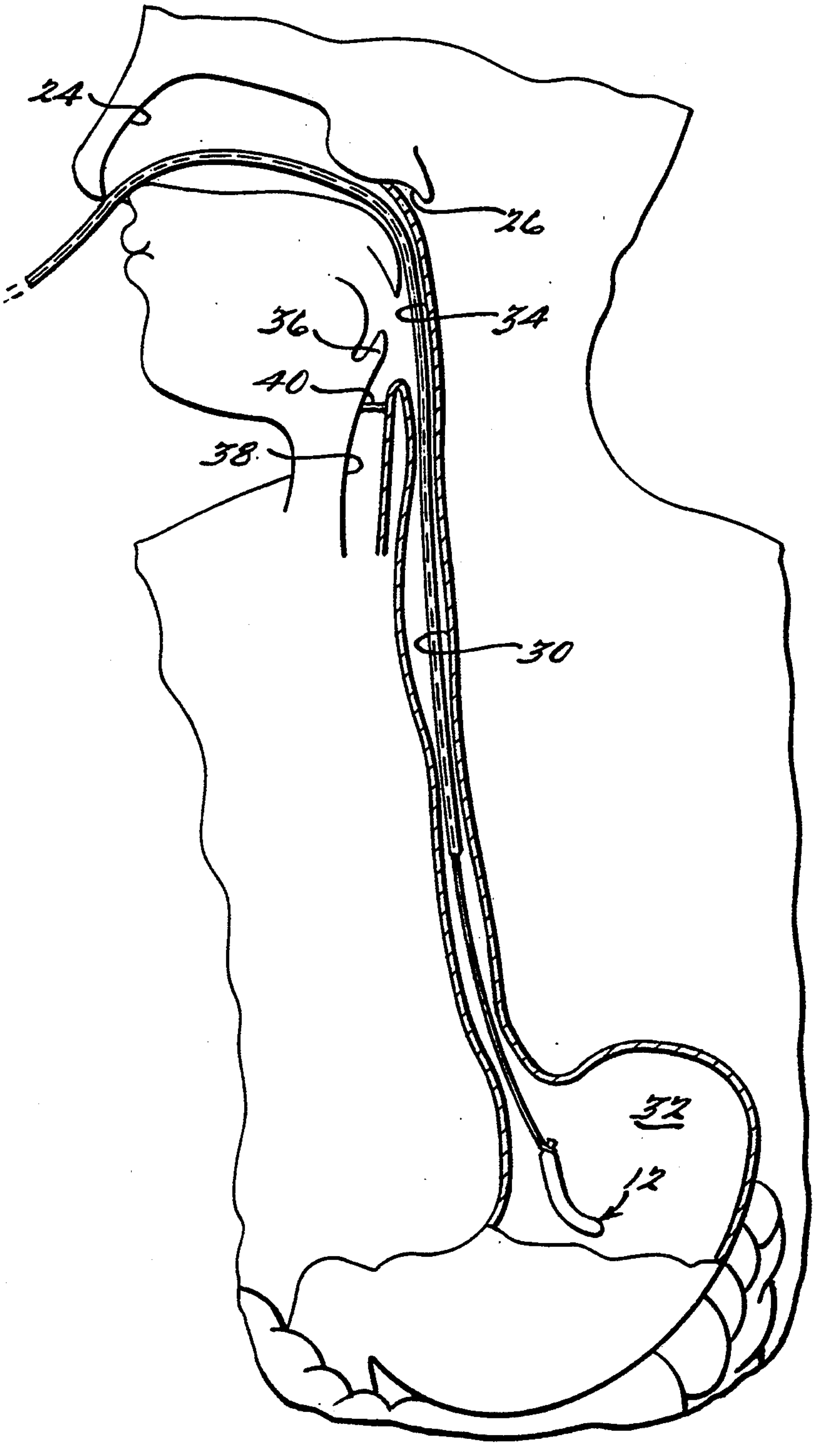
FIG. 2 is the system of FIG. 1 wherein the weight has been swallowed and the guide string has been routed through the nostril, nasopharynx, oropharynx, and esophagus, and the nasogastric tube is being inserted, guided by the guide string.

The preferred method of inserting the nasogastric tube 16 is illustrated in FIG. 2. The weight 12 is inserted through a nostril 24 into the nasopharynx 26, keeping a free end 28 of the guide string 14 outside the patient. The patient swallows the weight 12, carrying it through the esophagus 30 to the stomach 32.

Once the weight 12 and guide string 14 are in place, the free end 28 of the guide string 14 is inserted through the aperture 22 at the tip of the insertion end 18 of the nasogastric tube 16. The nasogastric tube 16 is then inserted into the nostril 24, through the nasopharynx 26, oropharynx 34, and esophagus 30, and into the stomach 32, at all times following the guide string 14 through the otherwise difficult-to-negotiate passageways 24, 26, 30, & 34. The guide string 14 ensures that the nasogastric tube 16 will not bypass the epiglottis 36 into the trachea 38 and damage the vocal cords 40.

After the nasogastric tube 16 is withdrawn, the guide string 14 is cut and is drawn by peristaltic action through the esophagus 30 into the stomach 32. Both the weight 12 and the guide string 14 are digested easily and comfortably.

While the preferred embodiment of the invention has been disclosed, it should be appreciated that the invention is susceptible of modification without departing from the scope of the following claims.

I claim:

1. A system for introducing a nasogastric tube to the stomach of a patient comprising:

a digestible weight capable of being swallowed by the patient;

a digestible guide string having an insertion end portion attached to said weight and of a length commensurate with the distance between the patient's head and stomach, and having a free end portion of greater length than the insertion end portion and extending exteriorly of the patient's head; and a tube initially telescoped about the free end portion only of said guide string exteriorly of the patient, said tube being guidable by said guide string into the stomach of said patient subsequent to swallowing of said weight and the insertion end portion of said guide string by the patient, retraction of said tube from the patient conditioning said guide string and weight for digestion in the patient's stomach.

2. The system of claim 1, wherein said weight is of elongated cylindrical configuration.

3. A method for inserting a nasogastric tube into a patient's stomach comprising the steps of:

providing a weight having one end of a guide string attached thereto, inserting said guide string through a patient's nostril;

swallowing said weight and guide into the patient's stomach while maintaining a free end of the guide string exteriorly of the patient;

routing the free end of the guide string through a nasogastric tube;

guiding the nasogastric tube into the stomach along the guide string;

withdrawing only said nasogastric tube from the patient; and digesting said weight and string.

* * * * *